United States Patent [19]

Neenan et al.

[11] Patent Number: 4,892,975

[45] Date of Patent: Jan. 9, 1990

[54] DIETHYNYL MONOMERS AND POLYMERS THEREOF

[75] Inventors: Thomas X. Neenan, Arlington; George M. Whitesides, Newton, both of Mass.

[73] Assignee: President and Fellows of Harvard College, Cambridge, Mass.

[21] Appl. No.: 101,632

[22] Filed: Sep. 28, 1987

[51] Int. Cl.$^4$ .................... C07C 149/34; C07C 43/29; C07C 25/28

[52] U.S. Cl. ...................... 568/56; 568/639; 570/128

[58] Field of Search .................. 568/56, 639; 570/128, 570/182

[56] References Cited

U.S. PATENT DOCUMENTS

| | | | |
|---|---|---|---|
| 3,714,276 | 1/1973 | Pierce et al. | 568/812 |
| 4,097,460 | 6/1973 | Jabloner | 526/90 |
| 4,301,313 | 11/1981 | Marshall et al. | 570/128 |

OTHER PUBLICATIONS

M. Ballester et al., Tetrahedron Lett. 1977, (27), 2353–4.

Waugh et al., J. Organometallic Chem., vol. 39, pp. 275–278 (1972).

Coe et al., J. Chem. Soc. (C), 1967, pp. 2626–2628.

*Primary Examiner*—Mary E. Ceperley

[57] ABSTRACT

The compound 1,3-diethynyl tetrafluorobenzene, and compounds having the structure

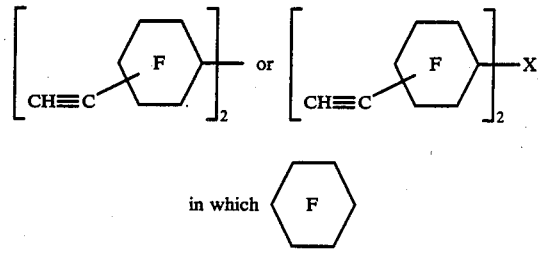

represents a perfluorinated benzene ring and X represents oxygen or sulfur, as well as homopolymers and copolymers thereof.

2 Claims, No Drawings

DIETHYNYL MONOMERS AND POLYMERS THEREOF

This invention described herein was made with Government support and the U.S. Government has certain rights in the invention.

This invention relates to novel diethynyl perflourinated aromatic monomers and to polymers and copolymers thereof.

It has hitherto been proposed in Jabloner U.S. Pat. No. 4,097,460 to make certain aryl acetylenes and polymers thereof, and in Pierce et al., U.S. Pat. No. 3,714,276, there has been described 1,3-divinyl tetrafluorobenzene. It has also been proposed in Waugh et al., J. Organometallic Chem., Vol. 39, 275–278 (1972) to make 1,4-diethynyl tetrafluorobenzene and certain other ethynyl substituted perfluorinated aromatic compounds, but there was no indication that such compounds could be polymerized.

It has now been found that 1,3-diethynyl tetrafluorobenzene can be synthesized and can be polymerized and copolymerized to form cross-linked polymers and copolymers having unique properties. It has also been found that compounds having the structure

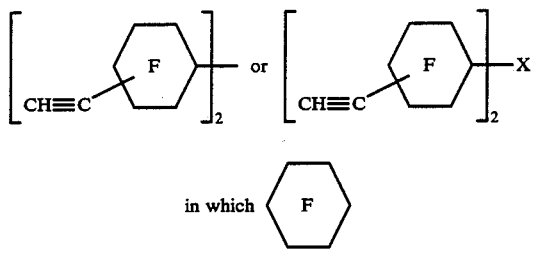

in which $\langle F \rangle$ represents a perfluorinated benzene ring and X represents oxygen or sulfur, (that is, bis(ethynyl tetrafluorophenyl), as well as bis(ethynyl tetrafluorophenyl) ether and thioether) are monomers useful for making cross-linked polymers having analogous properties.

The monomers of the present invention are useful in making polymers and copolymers which are characterized in general by being cross-linked, resistant to oxidation and pyrolysis at elevated temperatures, soluble in organic solvents such as dioxane, 1,2-dichlorobenzene, and the like, having good tribological characteristics (surface slipperiness) and low dielectric constant as well as high hardness, and capable of being readily molded at elevated temperature and pressure. The polymers may be homopolymers and they may, if desired, be end capped or copolymerized with monoethynyl tetrafluorobenzene or other monoethynyl perfluorinated aromatic monomer provided the amount of the selected 1,3-diethynyl tetrafluorobenzene monomer or of the selected bis(ethynyl tetrafluorophenyl) or bis(ethynyl tetrafluorophenyl) ether or thioether monomer is at least 50% by weight of the total acetylenic monomer present in the polymerization mixture. Copolymers of the monomers with each other or with other mono-or di-ethynyl or vinyl compounds can also be made, preferably containing 50% by weight or more of the selected monomer. The polymers are useful in packaging or sealing such products as electronic chips, biomedical materials, and as general purpose synthetic resins.

1,3-diethynyl tetrafluorobenzene can be prepared from 1,3-diiodo- or 1,3-dibromotetrafluorobenzene by reaction with trimethylsilyl acetylene in the presence of palladium and copper complex catalysts, then converting the resulting trimethylsilyl-substituted ethynyl derivatives to ethynyl derivatives by alkaline ester interchange with methyl alcohol. The monomers containing two aromatic rings can be prepared by first converting the appropriate dibromo or diiodo tetrafluoro benzene or a mixture thereof to the corresponding substituted biphenyl or bis(substituted phenyl) ether or thioether by conventional methods, then treating the product as described above for the preparation of the 1,3-diethynyl tetrafluorobenzene, or by using hydroxypropyl substituted acetylene (2-methyl-3--butyn-2-ol) in place of trimethyl silyl substituted acetylene.

The monomers can be polymerized in solution, for example in dioxane, in the presence of oxygen and a copper complex catalyst at temperatures from approximately 50° to approximately 100° C. The monoethynyl perfluorinated benzene employed for end capping the polymer can be mixed with the difunctional monomer at the beginning of the polymerization reaction provided the amount of the monofunctional monomer is less than 50% by weight of the total monomer. The monomers can also be polymerized in a cyclotrimerization polymerization in solution in the presence of a Ziegler-Natta catalyst such as diethyl aluminum chloride and titanium tetrachloride at a temperature in he approximate range −20° to 40° C.

The following specific examples are intended to illustrate more fully the nature of the invention without acting as a limitation upon its scope.

In the procedures described, all reactions for the preparation of ethynyl monomers were carried out under an atmosphere of argon in order to avoid premature polymerization.

Melting points were determined on a Thomas Hoover melting point apparatus and are uncorrected. Infrared spectra were recorded as KBr discs or as thin films on NaCl plates. $_1$H NMR spectra were recorded at 80 MHz or 300 MHz. Mass spectra were recorded at 70 eV or by GC/MS using a HP 5990A. Diisopropylamine was distilled from KOH before use. Diethyl ether and tetrahydrofuran (THF) were distilled from disodium benzophenone dianion before use.

EXAMPLE 1

Synthesis of 1,3-diiodotetrafluorobenzene

To a cooled solution of conc. H$_2$SO$_4$ (50 mL) was added in portions periodic acid (7.5 g, 33 mmol). To this clear solution was added in portions finely ground KI (16.43 g, 100 mmol), whereupon an exothermic reaction took place with the evolution of iodine vapor and the formation of a dark solution. 1,2,3,5-Tetrafluorobenzene (5 g, 33 mmol) was added dropwise and the reaction mixture was heated to 70° C. for 4 hours. Upon cooling, the solution was poured carefully onto crushed ice (200 g) and filtered to remove excess iodine. The filtrate consisted of an orange aqueous layer and a heavy dark oil. Diethyl ether (200 mL) was added to dissolve the oil and the organic layer was separated, and washed with 10% sodium thiosulfate solution, followed by washing with water and drying. The solvent was removed to yield an orange oil which was further purified by passing it through a short column of silica gel, using n hexane as the eluting solvent. Removal of the solvent yielded 1,3-diiodotetrafluorobenzene (7.1 g) as a colorless liquid in 61% yield (based on 85% pure starting material 1,2,3,5 tetrafluorobenzene); bp 140° C. (13 torr). Mass spectrum (EI) m/z (relative intensity) 402 (M+, 37), 275 (72), 254 (5.4), 148 (100), 129 (9.3), 127 (54.8), 110 (6.0). Anal. calcd for $C_6F_4I_2$: C, 17.91; I, 63.18. Found: C, 17.52; I, 63.18.

Synthesis of 1,3-bis((trimethylsilyl)ethynyl)tetrafluorobenzene

To a solution of 1,3-diiodotetrafluoroenzene (2) (52.0 g, 130 mmol) in freshly distilled diisopropylamine (600 mL) was added dichlorobis(benzonitrile) palladium (1.68 g, 2.4 mmol), triphenylphosphine (1.26 g, 4.8 mmol) and copper (II) acetate hydrate (0.47 g, 2.4 mmol). The solution was degassed by passing a rapid stream of argon through it. (Trimethylsilyl) acetylene (TMSA) (28 g, 2 2 equiv) was added over 1 h at room temperature to the clear yellow green solution. The solution changed color rapidly to a yellow brown with the formation of a heavy precipitate. The solution was heated at reflux until GC analysis indicated that all starting material had disappeared, approximately 6 hours. The solution was allowed to cool to room temperature and was filtered to remove the precipitate of diisopropyl ammonium bromide salts. The solvent was removed at reduced pressure and the residue was taken up in methylene chloride. Extraction with 5% HCl followed by extraction with water (twice), drying of the organic layer and removal of the solvent yielded the crude product as a dark oil. The oil was taken up in the minimum amount of hexanes (20 mL) and applied to a silica gel column (200 g) packed in hexanes. Elution with hexanes removed first 1,4-bis(trimethylsilyl) butadiene (0.65 g) followed by the desired 1,3-bis((trimethylsilyl)ethynyl)tetrafluorobenzene as colorless crystals in 92% yield; mp 55°–57° C. IR (KBr), 2980, 2920, 2080, 1505, 1260, 990, 850 cm$^{-1}$. $_1$H NMR (80 MHz, CDCl$_3$0.28 (s); Mass spectrum (EI) m/z (rel. intensity) 342 (M+,22.4), 327 (100), 156 (10.7); Anal. Calcd for $C_{16}H_{18}F_4Si_2$: C, 56.14; H, 5.26. Found: C, 56.34; H, 5.34.

1,3-Diethynyltetrafluorobenzene

To a solution of 1,3-bis((trimethylsilyl) ethynyl)-benzene (34.2 g, 100 mmol) in degassed methanol (400 mL) was added KOH (28 mg, 0.5 mmol) in 1 mL of water. The solution was stirred at room temperature for 20 min. when GC analysis indicated that the reaction was complete. The reaction mixture was diluted with water (500 mL) and extracted with n-pentane until the extracting solvent was free of product. The combined organic layers were dried over magnesium sulfate and the solvent removed at reduced pressure at room temperature. The residue was distilled at 55° C. and 1.0 torr to yield 1,3-diethynyltetrafluorobenzene (18.0 g, 91%) as a colorless liquid. IR (film on NaCl) 3300, 130, 1480 cm$^{-1}$. $_H$NMR (80 MHz, CDCl$_3$) 3.50 (s, 2 H); Anal. Calcd. for $C_{10}H_2F_4C$, 60.60; H, 1.01. Found: C, 60.68; H, 0.94.

EXAMPLE2

Synthesis of Poly(1,3-diethynyltetrafluorobenzene)

A 4 necked 3000 mL round bottomed flask fitted with a reflux condenser, a gas inlet tube, a thermometer and an addition funnel was charged with a mixture of p-dioxane (1000 mL) and pyridine (100 mL). To this mixture was added CuCl (0.78 g, 8 mmol) and 1.16 g, 10 mmol) N, N', tetramethylethylene diamine (TMEDA). Oxygen was bubbled through the solution while the temperature was gradually raised to 60°–65° C. To the deep blue green solution was added a mixture of 1,3-diethynyl-tetrafluorobenzene (40 g, 200 mmol) and, as an end capping or copolymerizing monofunctional monomer, monoethynylpentafluorobenzene (15.36 g, 80 mmol) in p-dioxane (200 mL). The temperature rose to 75° C. Heating was continued at this temperature for 2 hours and the reaction mixture was then allowed to cool to room temperature. Oxygen addition was continued for a further 4 hours, whereupon a white precipitate gradually separated from solution. The solvent volume was reduced to half by means of a rotary evaporator and the residual mixture was poured into a rapidly stirred mixture of methanol (1500 mL) containing 15 mL of concentrated hydrochloric acid. The crude product precipitated as a heavy off-white powder which was recovered by filtration. The product was thoroughly washed with water (1000 mL), followed by washing with methanol (500 mL), and was further purified by dissolving in toluene (800 mL) and drying the solution by means of the addition of magnesium sulfate. The solution was filtered and the filtrate was treated with ethylene diamine (5 mL), then heated to 70° C. under nitrogen and maintained at this temperature for twenty minutes. The solution was hot filtered to remove a deep blue precipitate of copper salts, then was cooled and extracted with 5% HCl (3×200 mL) followed by extraction with distilled water (3×200 mL). The polymer solution was concentrated to 300 mL under reduced pressure and the product recovered as before by pouring the mixture into methanol (1000 mL) to precipitate the polymer. The product was collected by filtration and washed successively with diethyl ether (200 mL) and n-pentane (200 mL). The final product was a off white non-melting powder. A total of 38.6 g (69.6%) of product was recovered. IR (NaCl) 2220 (w), 1620 (s), 1520 (s), 1480 (vs), 1400 (s), 1120 (s), 990 (m) 965 (vs), 910 (m). $^{19}$F NMR (p-dioxane-d8) 220.4, 202.4, 190.8, 176.1, 164.4, 163.9. Calcd. for DP=5, C, 58.14, H, 0.00, F, 41.85. Found: C, 58.23; H, 0.33; F, 37.14. The product was capable of being molded at temperatures from 40° to 150° C. at moderate (up to 10,000 psi) pressures. In contrast, the polymer of 1,4 diethynyl tetrafluorobenzene made under the same conditions was rigid and brittle and incapable of being molded under such conditions. In addition, the polymer of the 1,3-difunctional monomer was soluble in dioxane and in 1,2-dichlorobenzene, whereas the 1,4-difunctional polymer was essentially insoluble in such solvents.

EXAMPLE 3

Bis(4,4'-dibromo tetrafluorophenyl)sulfide

A solution was prepared of 1,4-dibromotetrafluorobenzene (20 g, 65 mmol) in a mixture of n-hexane and diethyl ether (3:2 v/v) (500 mL). The solution was cooled to −78° C. and to this solution was added n-butyllithium (1 equiv, 40 mL of a 1.6M solution) dropwise over 30 min. The resulting yellow solution was stirred at −78° C. for 3 h. To this solution was added sulfur dichloride (SCl$_2$) (0.5 equiv, 3.35 g, 33 mmol) dropwise in one portion over 5 min. The solution was stirred at −78° C. for a further 1.5 hours and then allowed to warm to room temperature. Water (10 mL) was added and the solution was allowed to stand overnight. The yellow solution was extracted with water (3×300 mL) and dried (M$_g$SO$_4$). The solvent was removed to yield an oily yellow solid, which was dissolved in n-hexane and passed through a short column of silica; the solvent was removed to yield the product as white cubic crystals. A total of 10 g (62%) of the desired product was recovered. The melting point was 105°–107° C. IR (KBr) 1450, 1240, 940, 790; Mass Spectrum (EI), (Rel. intensity) 490 (53.8), 488 (100), 486 (50.7), 409 (12.3), 407 (11.3), 328 (23.1). Anal. Calcd. for $C_{12}Br_2F_8S$: C, 29.63, F, 31.27. Found: C, 29.61; F, 30.70.

Synthesis of (4,4'-bis(3-hydroxy-3-methyl-1-butynyl) tetrafluorophenyl) sulfide To a solution of bis(4,4'-dibromo tetrafluorophenyl) sulfide (4.86 g, 10 mmol) in dry deoxygenated diisopropylamine was added dichlorobis(triphenylphasphine) palladium (700 mg, 1 mmol) and copper (1) acetate (200 mg, 1 mmol). The solution was cooled by means of an ice bath and to the cooled solution was added 2-methyl 3-butyn 2-ol (2.13 g, 25 mmol). The solution was allowed to warm to room temperature over a period of 1 hour and was then heated at reflux for a period of 24 hours. The solution was cooled and filtered to remove the precipitate of diisopropylammonium bromide. The residue was dissolved in methylene chloride, extracted with water, the organic layer was dried (magnesium sulfate), and the solvent removed. The residue was chromatographed on silica gel using diethyl ether/hexane (3:7 v/v) as the eluent. A white crystalline compound was removed from the column which was identified by mass spectrometry as 1,4-bis-(3-hydroxy 3-methyl-1-butynyl)tetrafluorobenzene. Further elution with diethyl ether/hexane (1:1 v/v) then yielded the desired product as pale yellow crystals. The yield was 2.2 g (44.5%), mp 148–150 C. IR (KBr) 3300, 2980, 2220, 1360, 1190, 1150, 975, 940 $cm^{-1}$. $^1H$ NMR (80 MHz, $d_6$-acetone) $\delta 2.8$(s, 2H), 1.55(s, 12H); Mass Spectrum (E1)(rel. intensity) 494 (1.0), 479 (0.3), 262 (100). Anal. Calcd. or $C_{22}H_{14}F_8O_2S$: C, 53.44; H, 2.83. Found: C, 53.87, H, 2.62.

Synthesis of (4,4'-diethynyloctafluorophenyl) sulfide

This compound was prepared by the basic hydrolysis of (bis-4,4'(3-hydroxy-3-methyl-1-butynyl)octafluorophenyl) sulfide using a procedure analogous to the preparation of 1,4-diethynyloctafluorobiphenyl described above. From 4 g of starting material there was obtained 223 g (73%) of product as tan colored crystals. IR(KBr) 3320, 2110, 1480, 1190, 1160, 980, 960 $cm^1H$ NMR ($CDCl_3$) $\delta 3.82$(s). Mass Spectrum (E1) (rel. intensity) 378 (2.0), 354 (100). Anal. Calcd or $C_{16}H_2F_8S$: C, 50.79; H, 0.71. Found: C, 51.03; H, 0.82.

EXAMPLE 4

Synthesis of poly(bis(4,4'-diethynyltetrafluorophenyl) sulfide)

A 4 necked 1000 mL round bottomed flask fitted with a reflux condenser, a gas inlet tube, a thermometer and an addition funnel was charged with a mixture of p-dioxane (500 mL) and pyridine (20 mL). To this mixture was added CuCl (0.20 g, 2 mmol) and 0.29 g, 2.5 mmol) of TMEDA. Oxygen was bubbled through the solution while the temperature was gradually raised to 60°–65° C. To the deep blue-green solution was added a mixture of bis(4,4'-diethynyltetrafluorophenyl) sulfide (3.78 g, 10 mmol) and monoethynylpentafluorobenzene (0.96 g, 5 mmol) in p-dioxane (30 mL). The temperature rose to 70° C. Heating was continued for 2 hours and the reaction mixture was allowed to cool to room temperature. Oxygen addition was continued for a further 3 hours. The solvent volume was reduced to one third by means of a rotary evaporator and the residual mixture was poured into a mixture of rapidly stirring methanol (200 mL) containing 2 mL of concentrated hydrochloric acid. The crude product precipitated as a heavy off-white powder which was recovered by filtration. The product was thoroughly washed with water (500 mL), followed by washing with methanol (300 mL). The polymer was dissolved in toluene (200 mL) and the solution was dried by means of the addition of magnesium sulfate. The solution was filtered and the filtrate was treated with ethylene diamine (2 mL), then heated to 70° C. under nitrogen and maintained at this temperature for fifteen minutes. The solution was hot filtered to remove a small amount of precipitated copper salts, cooled, and extracted with 5% HCl (two 200 mL portions) followed by extraction with distilled water (three 200 mL portions). The polymer solution was concentrated to 100 mL under reduced pressure and the product recovered as before by precipitation of the mixture into methanol (400 mL). The product was collected by filtration and washed successively with diethyl ether (200 mL) and n-penane (200 mL). A total of 3.5 g (73.8%) of product was recovered. IR (NaCl) 2230 (m), 1625 (s), 1530 (s), 1470 (s), 1220 (s), 990 (m), 940 (vs) $cm^{-1}$. Anal. Calcd. for $C_{32}F_{18}S$, C, 50.66, H, 0.00, F, 45.11. Found: C, 51.23; H, 0.39; F, 44.32.

EXAMPLE 5

Synthesis of 4,4'-bis(3-hydroxy-3-methyl-1-butynyl)octafluorobiphenyl

To a solution of 4,4'-dibromooctafluorobiphenyl (10 g, 21.9 mmol) in degassed diisopropylamine (350 mL) was added dichlorobis(triphenylphosphine) palladium (770 mg, 1.05 mmol, 5 mol %) and copper (1) acetate (219 mg, 1.05 mmol, 5 mol %). The solution was cooled to 0° C. and to this solution was added 2-methyl-3-butyn-2-ol (2.2 equivalents, 4.0 g, 4.7 mL). The solution was allowed to warm to room temperature and was subsequently heated at 50° C. for 12 hours. The solution was cooled and filtered to remove the precipitate of diisopropylammonium bromide. The solvent was removed at reduced pressure and the residue was chromatographed on a column of silica gel (200 g) packed with ethyl acetate. An oily yellow solid was removed from the column. The addition of a couple of drops of methanol caused the oil to solidify. The resulting solid was recrystallized from a mixture of ethyl acetate/hexane (1:2) to yield 4,4'-bis(3-hydroxy-3-methyl-1-butynyl) octafluorobiphenyl as white crystals. The yield was 8.6 (92%), mp 119°–121° C. IR (KBr) 3400, 2960, 1475, 1365, 1210, 1170, 990, 962 $cm^{-1}$. $^1H$ NMR (80 MHz, $CDCl_3$) $\delta 2.7$ (s, 2H), 1.53 (s, 12H); Mass Spectrum (E1)(rel. intensity) 462 (3.7), 447 (44.0), 432 (1.5); Anal. Calcd for $C_{22}H_{14}F_8O_2$: C, 57.14; H, 3.03. Found: C, 60.60; H, 4.78.

Synthesis of 4,4'-diethynyloctafluorobiphenyl

A solution of the compound described above (7.0 g, 15.1 mmol) was prepared in freshly distilled toluene. The resulting solution was deoxygenated with dry nitrogen and to this solution was added powdered KOH (1.0 g, 16.6 mmol). The solution was heated at reflux for 1 hour and the evolution of acetone was monitored by GC. The resulting dark solution was cooled to room temperature and the toluene was removed. The dark residue was dissolved in the minimum amount of methylene chloride and passed through a short column of silica. The solvent was removed from the pale yellow eluent to yield 4,4'-diethynyloctafluorobiphenyl as a off white solid. The yield was 4.6 g, (84.0%). IR (KBr) 3300, 2100, 1620, 1465, 1385, 1270, 990, 719, 670 cm$^{-1}$. $_1$H (80 MHz, CDCl$_3$) 3.75 (s); Mass Spectrum (El)(rel. intensity) 322 (100), 253 (27.6); Anal. Calcd. for C$_{16}$H$_2$F$_8$: C, 55.49; H, 0.57. Found: C,55.32; H, 0.95.

EXAMPLE 6

Synthesis of Poly(4,4'-diethynyloctafluorobiphenyl)

A 4-necked 1000 mL round bottomed flask fitted with a reflux condenser, a gas inlet tube, a thermometer and an addition funnel was charged with a mixture of p-dioxane (500 mL) and pyridine (20 mL). To this mixture was added CuCl (0.39 g, 4 mmol) and TMEDA (0.58 g, 5 mmol). Oxygen was bubbled through the solution while the temperature was gradually raised to 60°-65° C. To the deep blue-green solution was added a mixture of 4,4'-diethynyloctafluorobiphenyl (5.9 g, 17 mmol) and monoethynylpentafluorobenzene (1.56 g, 8 mmol) in p-dioxane (50 mL). The temperature rose to 75° C. Heating was continued for 2 hours and the reaction mixture was allowed to cool to room temperature. Oxygen addition was continued for a further 4 hours. A white precipitate gradually separated from solution. The solvent volume was reduced to one third by means of a rotary evaporator and the residual mixture was poured into a mixture of rapidly stirring methanol (600 mL) containing 5 mL of concentrated hydrochloric acid. The crude product precipitated as a heavy off-white powder which was recovered by filtration. The product was thoroughly washed with water (1000 mL), followed by washing with methanol (500 mL). The polymer was dissolved in toluene (300 mL) and the solution dried by means of the addition of magnesium sulfate. The solution was filtered and the filtrate was treated with ethylene diamine (5 mL). The solution was heated to 70° C. under nitrogen and maintained at this temperature for twenty minutes, after which it was hot filtered to remove a deep blue precipitate of copper salts. The solution was then cooled and extracted with 5% HCl (three 200 mL portions) followed by extraction with distilled water (three 200 mL portions). The polymer solution was concentrated to 100 mL under reduced pressure and the product recovered as before by precipitation of the mixture into methanol (1000 mL) and filtration, and washed successively with diethyl ether (200 mL) and n-pentane (200 mL). A total of 6.2 g (82.6%) of product was recovered. IR (NaCl) 2220 (w), 1620 (s), 1530 (s), 1470 (vs), 1380 (s), 1220 (s), 990 (m), 960 (vs), cm$^{-1}$ Anal. Calcd for C$_{32}$F$_{18}$, 52.89, F, 47.10. Found: C, 51.98; F, 46.66.

What is claimed is:

1. The compound 1,3-diethynyl tetrafluorobenzene.
2. A compound having the structure

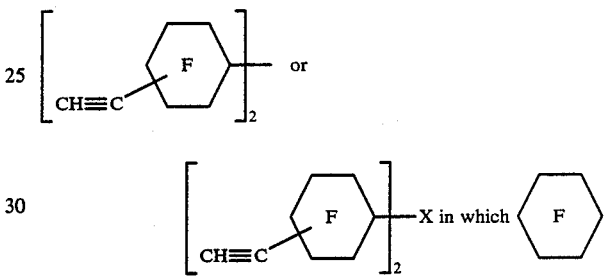

represents a perfluorinated benzene ring and X represents oxygen or sulfur.

* * * * *